(12) United States Patent
Goodman

(10) Patent No.: US 12,311,074 B1
(45) Date of Patent: *May 27, 2025

(54) BURN WOUND TREATMENT

(71) Applicant: Marie's Original Formulas LLC, Pearl River, NY (US)

(72) Inventor: Zalman Goodman, Monsey, NY (US)

(73) Assignee: Marie's Original Formulas LLC, Pearl River, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/962,073

(22) Filed: Nov. 27, 2024

(51) Int. Cl.
*A61L 26/00* (2006.01)
*A61K 9/00* (2006.01)

(52) U.S. Cl.
CPC ........ *A61L 26/0066* (2013.01); *A61K 9/0017* (2013.01)

(58) Field of Classification Search
CPC .......................... A61L 26/0066; A61K 9/0017
See application file for complete search history.

(56) References Cited

U.S. PATENT DOCUMENTS

| | | |
|---|---|---|
| 2007/0224271 A1 | 9/2007 | Marraccini |
| 2013/0060208 A1 | 3/2013 | Givskov et al. |
| 2014/0276493 A1 | 9/2014 | Leung et al. |

FOREIGN PATENT DOCUMENTS

| | | |
|---|---|---|
| JP | 6847569 | 3/2021 |

OTHER PUBLICATIONS

Rienhrardt et al, "A Topical Wound Disinfectant (ETacridine Lactate) Differentially Affects the Production of Immunoregulatory Cytokines in Human Whole Cell Cultures" HMP Global (Year: 2024).*
Chandan K. Sen, "Human Wound and Its Burden: Updated 2020 Compendium of Estimates," Wound Healing Society, Feb. 14, 2021.
Harris-Tryon et al., "Microbiota and Maintenance of Skin Barrier Function," https://www.science.org/doi/10.1126/science.abo0693, Dec. 21, 2023.
Swaney et al., "Living in Your Skin: Microbes, Molecules, and Mechanisms," American Society for Microbiology, Apr. 2021.
Linehan et al., "Non-classical Immunity Controls Microbiota Impact on Skin Immunity and Tissue Repair," Elsevier Inc., Feb. 8, 2018.
Thiboutot et al., "Keeping the peace: commensal Cutibacterium acnes trains CD4+ TH17 cells to trap and kill," https://doi.org/10.1172/JCI145379, 2021.
Alakomi et al., "Lactic Acid Permeabilizes Gram-Negative Bacteria by Disrupting the Outer Membrane," Applied and Environmental Microbiology, May 2000.
Lin et al., "Zinc in Wound Healing Modulation," www.mdpi.com/journal/nutrients, 2018.
Reinhardt et al., "A Topical Wound Disinfectant (Ethacridine Lactate) Differentially Affects the Production of Immunoregulatory Cytokines In," HMP Global, 2024.
Canchy et al., "Wound Healing and Microbiome, An Unexpected Relationship," https://doi.org/10.1111/jdv.18854, 2023.
"Fourteenth Annual Meeting and Exhibition of the Wound Healing Society," Wound Repair and Regeneration, 2004.
Pasquet et al., "The Contribution of Zinc Ions to the Antimicrobial Activity of Zinc Oxide," Elsevier B.V., Sep. 2014.
Pramod et al., "Natural Product Communications", 2010, vol. 5, pp. 1999-2006, Year: 2010.
LibreTexts Chemistry 4.1: "Molecular Weight of Polymers", https://chem.libretexts.org/bookshelves/organic_chemistry/polymer_Chemisry_(Schaller)/04%3A_Polymer_Properties/4.01%3A_Molecular_Weight; Downloaded Nov. 2024, Year: 2024.
Buret, "Canadian Journal of Veterinary Research", Jan. 2010, vol. 74, pp. 1-10 Year: 2010.
Reinhardt et al., "Wounds, A Compendium of Clinical Research and Practice", Aug. 2005, vol. 17, pp. 213-221, Year: 2005.
Bakhtar, "Iran Journal of Public Health", Nov. 2013, vol. 42, pp. 1327-1328, Year: 2013.
Lee et al., "Frontiers in Pharmacology," Oct. 2019, vol. 10, pp. 1-10 Year: 2019.
Quora, "Is It Okay To Apply Powder After Moisturizer?" 2024 with postings from 4, 6 Or 7 years before Mar. 2024, https:/www.quora.com/is-it-okay-to-apply-powder-after-moisturizer, Year: 2024.
Khalil et al., "Royal Society of Chemistry," 2017, vol. 7, pp. 32669-37681, Year: 2017.
Ranzato et al., "Journal of Ethnopharmacology," 2011, vol. 134, pp. 443-449, Year: 2011.

* cited by examiner

*Primary Examiner* — Carlos A Azpuru
(74) *Attorney, Agent, or Firm* — Weiss & Arons LLP

(57) ABSTRACT

Compositions and methods for treatment of burns and other wounds. A unitary product containing all ingredients of the compositions may deliver composition ingredients to a surface of a burn/wound treatment site. The unitary product may include an ointment. The unitary product may include a cream. The unitary product may include a hydrogel. The compositions may include antibiotic ethacridine lactate. The compositions may include metal-containing species. The compositions may include a moisture-modulating agent. The compositions, when applied to the site, may constitute a barrier overlying the surface. The unitary product may deliver the antibiotic onto the surface. The unitary product may deliver the metal-containing species onto the surface. Each of the antibiotic and the metal-containing species may positively modulate wound bed and perilesional cellular processes supportive of healing. Initial testing and use studies have yielded good wound closures, with minimal-to-no scarring and high regain of function of repaired tissues.

21 Claims, No Drawings

BURN WOUND TREATMENT

FIELD OF TECHNOLOGY

Aspects of the disclosure relate to treatment of traumatized skin regions. In particular, the disclosure provides compositions of treatments, and methods for treatment, of a variety of burns (including thermal burns and radiation burns) and other wounds (including open wounds of diabetic/vascular ulcers and surgical/traumatic avulsions).

BACKGROUND OF THE INVENTION

Burn wounds and other open wounds may cause patients discomfort, disfigurement, severe pain and even death. Such wounds (hereinafter, in the alternative, "burns/wounds" or singular "burn/wound"), inadequately attended, may progressively degrade patients' quality of life. Therefore, timely and effective treatment of burns and other open wounds may be vital to patients' outcomes.

However, such burns/wounds present significant treatment challenges to wound care clinicians. Some particularly difficult challenges may directly contribute, as per analysis of a 2014 United States data set, to approximately 8,200,000 Medicare beneficiaries suffering from chronically non-healing/non-closing open wounds. (Sen C K (2021) Human Wound and Its Burden: Updated 2020 Compendium of Estimates. *Advances In Wound Care* 10:281)

While difficult-to-treat open wounds such as diabetic foot ulcers and skin lesions from venous deficit may be predominant in the Medicare-age elderly population, challenging open wound sites such as from moderate-to-severe thermal burns, radiation therapy, surgical excision, and lacerations (from, e.g., home/work/recreation accidents; disaster/terror/combat wounds) are prevalent throughout all age demographics.

In the United States, frequency of thermal burn wounds of sufficient severity to warrant emergency/urgent care are estimated at ~600,000 cases per annum. (Ivanko A, Garbuzov A E et al. (2024) The Burden of Burns: An Analysis of Public Health Measures. *Journal of Burn Care & Research* 45:1095) Such thermal burns often present as open wounds, with severe disruption of skin integrity and damage to underlying dermal and hypodermal/subcutaneous regions. These burns may typically require urgent attention to cleansing, disinfection, debridement, medicament application and dressing.

Radiation burns represent an expanding modern-age category of traumatized tissue. According to the American Cancer Society (ACS), more than half of cancer patients undergo at least one round of radiation therapy. (ACS (2019) How Radiation Therapy Is Used to Treat Cancer.) An estimated 90%-95% of radiation therapy patients will present with radiation dermatitis. (Zasadziński K, Spałek M J, et al. (2022) Modern Dressings in Prevention and Therapy of Acute and Chronic Radiation Dermatitis—A Literature Review. *Pharmaceutics*. 14:1204) The presentation of radiation dermatitis burns—skin itchiness, inflammation, peeling, blistering and ulceration, potentially leading to open/necrotic wounds—may take several days, weeks, months and even years from a patient's radiation therapy. Radiated skin typically requires treatment well before external symptoms appear. Progression of severity of radiation burn symptoms may be improved by treatment well before, and continuing after, external symptoms of radiation dermatitis present.

Millions are impacted by other forms of dermatitis, such as atopic dermatitis, more commonly known as eczema. In the United States, eczema affects over 16 million adults and approximately 10 million children. While causation of atopic dermatitis is multi-factored, leading causes may be a weakened epidermal barrier and an overly primed immune system. Also prevalent are other forms of dermatitis, such as contact dermatitis triggered by contact with an environmental irritant and seborrheic eczema in sebaceous body regions. Outcomes of patients with those closed/non-open wound conditions may be improved by topical treatments. The same holds for patients with yet another closed/non-open wound condition, cellulitis, typically caused by infection beneath the epidermis by *Staphylococcus aureus*, a ground bacterium. Annual U.S. cellulitis cases are estimated at 14 million.

Serious challenges impede timely and effective treatment of burns/wounds. Several of the serious treatment challenges facing a wound care clinician may derive from conflicting therapeutic approaches being required simultaneously to effectively treat a burn or other wound. Two such significant conflicts are maintenance of wound site antiseptic sterility versus preservation of functionality of wound border skin microbiome and of functionality of wound bed tissue; and prevention of drying of the wound bed and/or of bordering perilesional tissue versus prevention of maceration. Achieving therapeutically optimized balances between such opposing clinical considerations is further complicated by the balances differing among wound types and, for a wound of a given type, changing with the wound's stage of healing.
Antiseptic Sterility Vs Microbiome Functionality Intact healthy skin normally presents against infection not only a mechanical barrier but also a bioactive barrier. Bioactivity is provided by commensal microbiota of the skin microbiome. The microbiota include numerous diverse types of viruses, fungi and bacteria. The latter constitute the bulk of the microbiome ecosystem. The microbiome ecosystem may differ and change according to body region characteristics (dry/moist/sebaceous) as well as according to degree of exposure to air and/or light.

By synthesizing and secreting specialized antimicrobial compounds, the skin microbiome biochemically thwarts attacks by agents of infection contacting the outer skin. And, as has become increasingly appreciated in the $21^{st}$ Century, the skin microbiome also dynamically affects lower-layer skin cells, modulating immunological and biosynthetic activities of dermal layers and also of hypodermal/subcutaneous layers, even as host cells reciprocally modify gene expression of the microbiota. (Harris-Tryon T A and Grice E A (2022) Microbiota and maintenance of skin barrier function. *Science* 376:940-945; Swaney M H and Kalan L R (2021) Living in Your Skin: Microbes, Molecules, and Mechanisms. *Infection and Immunity* 89(4):e00695-20)

A lesion of the skin's mechanical barrier—whether by physical trauma, heat, radiation, etc.—can give agents of infection access through the breach to exposed underlying tissue without the pathogens directly encountering the protective skin microbiome. In standard wound treatment practice, the lesion is, therefore, antiseptically cleansed and treated with antibiotics lethal to bacterial strains that cause infection, inclusive, inter alia, of *Staphylococcus aureus*. However, most antibiotics used in standard wound treatment practice also kill perilesional microbiome bacteria, inclusive, inter alia, of *Staphylococcus epidermidis* and *Cutibacterium acnes*, the predominant species of the microbiome bacterial component of most adult host body regions.

*Staphylococcus epidermidis* actively fights off *Staphylococcus aureus* by synthesizing and secreting antimicrobial molecules lethal to *S. aureus* but benign to the microbiome.

Other *S. epidermidis* secretions are credited with inhibiting biofilm formation by *S. aureus*, such biofilms capable of shielding film-covered pathogens from anti-pathogen molecules. Additionally, *S. epidermidis* strengthens skin cell-to-cell junctions, both by its own secretions and by stimulation of underlying host dermal layers. During neonatal development and beyond, *S. epidermidis* primes host T leucocytes against *S. aureus* while training those immune cells to accept the presence and functioning of the microbiome. Host dermal and immune cells previously induced and promoted by *S. epidermidis* seem to be actively influenced by the microbiota's responses to a breach of skin with the lesion's attendant chemical signals from exposed underlying tissues; those influenced host cells are strongly implicated in contributing directly to wound healing. (Canchy L, Kerob D, et al. (2023) Wound healing and microbiome, an unexpected relationship. *J European Academy Dermatology Venereology* 37(S3):7-15; Linchan J L, Harrison O J, et al. (2018) Non-classical Immunity Controls Microbiota Impact on Skin Immunity and Tissue Repair. *Cell* 172:784-796)

*Cutibacterium acnes* metabolizes sebum secretions of the sebaceous areas that the *bacillus* is typically associated with, such as hair follicles. *C. acnes* metabolites include low pH products (e.g., propionic acid) that help keep free of infection the direct access-way between outer and inner skin layers afforded by the hair follicles. *C. acnes* has been shown effective against MRSA, methicillin-resistant *S. aureus* not treatable by front-line antibiotics. *C. acnes* secretions also inhibit biofilm formation by *S. epidermidis*, a condition associated with *S. epidermidis* pathogenicity. Reciprocally, *S. epidermidis* secretions can inhibit pathogenetic biofilm formation by *C. acnes*. *C. acnes* also induces and promotes host T helper ($T_H$) cells that play a direct role in wound antiseptic cleansing. (Thiboutot D M and Nelson A M (2021) Keeping the peace: commensal *Cutibacterium acnes* trains $CD4^+$ $T_H$ 17 cells to trap and kill. *J Clinical Investigation* 131(2):e145379)

Application of broad-spectrum antibiotics to a patient's wound site may be deadly to the microbiome bacterial population of perilesional skin adjacent the site. Losses to the skin microbiome bacteria disrupts the complexly balanced local microbiome ecosystem. Losses to population of *S. epidermidis* and/or *C. acnes* and attendant disruption of the skin microbiome ecosystem along the wound border, impair the ability of the patient's wound border cells to properly execute pre-programmed highly coordinated rehabilitative functions. Those functions include covering the site with newly formed daughter cells that migrate away from parent border cells, swimming along and through moist fibroblast surfaces that begin to overlay the wound bed in response to biochemical signals produced by site-local host cells and perilesional microbiota.

Some of those daughter cells migrating from wound border tissue respond to other biochemical signals contributed to by perilesional microbiota and by oxygen-starved wound site cells, and differentiate into nascent vascular endothelium cells. Those proto-vascular cells build new capillary beds to supply blood and, thereby, oxygen to the wound site's "under construction" replacement tissue.

Other cells migrating inward from the wound border differentiate into myofibroblast cells. These "muscle-like" cells coordinate to tug on the border and on the new skin cells, drawing edges of the wound toward each other. The inward growing wound edges are pulled forward at rates and in concert with other concomitantly occurring cellular regrowth processes so as to foster scar-free wound closure.

Wound site cells and perilesional microbiota also produce biochemical signals that recruit macrophagic leukocytes to the wound site while simultaneously tamping down excess inflammation. The macrophages clean the wound site by attacking foreign invaders and eating away at and engulfing necrotic tissue, thus cleansing and debriding the site.

The above and other contributions of the perilesional microbiota to stages and processes of the body's highly coordinated healing responses are usually severely disrupted by the powerful antibiotics typically utilized in wound treatment to sterilize the wound site and prevent infection. Similarly, such antibiotics usually also negatively impact wound healing activities of wound bed cells, both those that are site-local—e.g., fibroblasts, nascent vascular endothelium cells, myofibroblasts—and the macrophages and other cells that are recruited to the wound bed.

Accordingly, it would be desirable to provide compositions and methods of application of the same, that yield antiseptic conditions on, and along the borders of, the wound bed and keep the regions free of infection, but without severely negatively impacting the perilesional skin microbiome or the wound bed cells. Such a balance can be had by use of effective antibiotics that are not powerful broad-spectrum drugs.

However, effective antibiotics that are not powerful broad-spectrum drugs may prove insufficiently lethal to the wide variety of pathogenic bacteria that may assault the wound's exposed tissues. Accordingly, to increase the antimicrobial reach and power of the compositions, it would be desirable that the compositions' non-broad-spectrum microbiome-preserving antibiotics be complemented by multiple other antimicrobial components friendly to the microbiome and wound bed cells. It would be desirable that those components be select natural products having centuries-long track records of experience-based safe use on the skin. It would be desirable, also, that those components have been widely, successfully and safely used as anti-infection preservative agents, now known to be distinguished for their antimicrobial properties.

It would also be desirable that components of the compositions be multi-modally stimulative of the body's natural healing processes, such as neovascularization and metalloprotease biosynthesis, as well as acting as antimicrobials.

Drying Vs Maceration

The wound site must be maintained moist to facilitate cell proliferation on the wound bed and along its perilesional borders, as well as to facilitate cellular migration along and through developing bed-covering biological surfaces. The proliferation and migration, coordinated with synchronized and targeted cellular differentiation, facilitate proper wound closure with limited scarring of and minimal functional loss to the repaired wound site. But excessive wetness, from exudate buildup and/or therapeutic application of aqueous treatments, may lead to tissues of the bed and borders becoming edematous and, thus, losing degrees of functionality required for healing. This concern may be heightened by such liquids being trapped on the wound site by an occlusive therapeutic covering. Yet occlusive coverings are needed to prevent evaporative drying of the wound site.

Accordingly, it would be desirable to provide compositions that, from a wet surface of the applied compositions most proximal to the burn/wound, deliver wound-drying agents (as well as antibiotic and immunomodulators, as above) to the wound beds of burns and other wounds; while also delivering rapid formation of occlusive coverings along the applied compositions' exposed surface farthest from and overlying the burn/wound, with progressively slowing increase of the coverings' depth into the bulk of the applied compositions. Rapid formation of the occlusive "top" coverings yields timely protection against wound fluid loss from the traumatized tissue of the wound, while the release, from the compositions' wet "bottom" surface, of drying agents onto the wound bed counters maceration.

Further to timeliness of therapeutic effect, it would be desirable, also, that the drying agents, immunomodulators, antibiotics and other antimicrobials be delivered in a unitary product together with the occlusives, to speed and case application of all components onto the burn/wound. Ease of application would render such product a boon to on-the-scene treatment of burns and other wounds, whether first aid is rendered by the patient or a first responder. Ease of application may also simplify clinical care for the patient, allowing for more frequent and/or less labor-intensive dressing changes.

BRIEF DESCRIPTION OF THE DISCLOSURE

Compositions and methods for treatment of burns/wounds are provided that may yield antiseptic conditions on, and along the borders of, the wound bed, keeping those regions free of infection, while not causing severe disruption of the perilesional skin microbiome or of the wound bed cells. Simultaneously, the compositions and methods may provide components to a burn/wound surface, which may dry the surface and also enhance wound healing through immunomodulation of perilesional microbiota and host cells. Simultaneously, the compositions and methods may provide occlusives to the burn/wound for rapid formation of an occlusive cover, giving the surface a protective anti-evaporation barrier.

Provided in the unitary product are the compositions' immunomodulators and moisture-modulating agents—including occlusives and such others as emollients and/or humectants—with the components being well tolerated compounds that have been used safely and studied for decades; in many cases, for centuries. Also provided in the unitary product is a mild antibiotic (relative to powerful broad-spectrum antibiotics), used as a wound disinfectant for over a century, in combination with natural products and natural-derived substances well known and long utilized in burn/wound and/or skin treatment for their antimicrobial disinfectant properties and their promotion of healing.

The compositions and methods for treatment of burns and other open wounds provided herein take advantage of recently characterized immuno-regulatory properties of composition components. Leveraging these properties may selectively promote natural healing processes—such as neovascularization, metalloprotease biosynthesis and macrophage recruitment—when most needed at various healing stages, while suppressing less desirable processes at most stages, such as inflammation.

The compositions and methods for treatment of burns and other wounds provided herein may also utilize to good effect interactions among composition components. For example, a drying agent blended into the unitary product is quite soluble in one of the product's emollients but not in any of its occlusives. The emollient "sweating out" of and away from the occlusives of the bulk of the applied compositions, may migrate not only the emollient but also the solubilized drying agent through the bulk of the compositions toward the burn/wound surface.

Thus, the unitary product may deliver the drying agents (as well as antibiotic and immunomodulators) from the wet surface of the applied compositions most proximal to the burn/wound, to the burn/wound surface; and also deliver rapid formation of the occlusive coverings along the applied compositions' exposed surface overlying and farthest from the burn/wound.

The compositions and methods for open wound treatment provided herein may also utilize to good effect synergies arising among composition components via protocol steps. For example, increased drying of the site contracts the wound bed, in turn raising the concentration of solubilized components, including those of drying agents, further desiccating the wound site. Of note is site-contraction increasing concentration of the antibiotic and other immunoregulators and, thereby, accelerating immunoregulation by them of wound healing processes.

The compositions may be used to perform steps of the methods. The methods may include administration of the compositions to a burn/wound site. The methods may include recurrent administration of the compositions to the burn/wound site over a course of its healing. The methods may include administration of the compositions to the wound by one or more than one wound clinician. The methods may include administration of the compositions to the wound by a first responder. The methods may include administration of the compositions to the wound by an untrained individual (such as a concerned citizen or even the wounded patient) with access to the compositions and associated use instructions, as may be had in an up-to-date first aid kit. Ease of application of the unitary product may allow for scheduling more frequent administrations (dressing changes, with preparation for and follow-up to the changes) than might be had with more complicated approaches.

Ethacridine lactate, an antibiotic ingredient of the compositions and methods, has been used clinically and studied for over a century. Low concentration ethacridine lactate was considered a useful disinfectant for much of that time, with its antibiotic and immunoregulatory properties becoming appreciated in recent decades.

A typical delivery form of ethacridine lactate used in wound healing is as 0.1% (wt/wt) solution, such as Rivinol®, available from CHEMAX PHARMA, Sofia, Bulgaria.

Another delivery form of ethacridine lactate used in wound healing is as dry yellow crystalline powder, such as that used, mixed with other ingredients, in ActXT Powder, developed by Maries Originals®, Pearl River, NY. Metal-species-containing ActXT Powder has been used to good effect as a cover overlying already applied Marie's Wounds & Burns Ointment with HydrOil Technology. The Marie's ointment forms an occlusive anti-evaporation cover over the burn/wound, while emollients pre-blended into the ointment solubilize active ingredients of the Marie's powder and transport them, across the occlusive layer and through the bulk of the applied ointment beneath the cover, to the wound bed. Such a two-step protocol of application of the Marie's ointment and then, after the occlusive cover forms, overlaying of that cover with the metal-species-containing Marie's powder, has been under scientific study in several clinical settings, with positive and yet further promising results.

Bakhtar (Amazing Topical Protocol and Novel Powder Dressing Combination Formula in Treatment of Diabetic Foot Wounds. (2013) *Iran J Public Health* 42:1327) alleges good results in treatment of diabetic ulcer a) by cleansing the wound with 0.1% ethacridine lactate solution and in combination with metronidazole, in normal saline; and b) by use of a "powder combination of ethacridine lactate (0.1%), zinc oxide, oak fruit and *Ginkgo biloba*" that was "sprinkled on wound" BID. The first Bakhtar result is unremarkable, as successful disinfectant use of low concentration ethacridine lactate solutions on open wounds has been well known since before 1920. The second Bakhtar result, also expected from well known properties of zinc oxide and of low concentration ethacridine lactate, does not present the novel principle of the Marie Original® two-step protocol outlined above. Nor does Bakhtar teach, explicitly or implicitly, this disclosure's combination, in a unitary ointment or cream product, of ethacridine lactate and a drying agent together with occlusives and other moisture-modulators.

The above embodiment of the invention of this disclosure teaches burn/wound treatment via an ointment or cream containing all the compositions' ingredients. Another embodiment of the invention, also presenting a barrier physiochemically protecting the burn/wound while delivering antibiotic and other active ingredients to the wound bed, involves a hydrogel. The hydrogel may include polymer chains that trap fluid within a hydrogel matrix.

Hydrogel polymer chains may be naturally derived. Naturally derived hydrogel polymer chains may include algae-derived polysaccharides. The naturally derived hydrogel polymer chains may include any other suitable naturally derived polymer chains. Any other suitable naturally derived polymer chains may include chitosan-derived polysaccharides. The hydrogel polymer chains may be synthetically derived. Synthetically derived hydrogel polymer chains may include poly(lactide-co-glycolide). The synthetically derived hydrogel polymer chains may include any other suitable synthetically derived polymer chains. Any other suitable synthetically derived polymer chains may include polyvinyl alcohol. The hydrogel polymer chains may include hybrids of naturally derived and synthetically derived polymer chains.

Hydrogel fluid is typically water but may include any other suitable fluid. Any other suitable fluid may include plasma. Any other suitable fluid may include plasma analogs. The plasma or plasma analogs may include cells or cell fragments such as platelets.

A hydrogel embodiment of the invention may include, loaded into the fluid, wound drying and immunomodulating agents, antibiotic including ethacridine lactate, and any other suitable species. Any other suitable species may include an emollient agent. Any other suitable species may include fibrin.

The hydrogel may be pre-made and may be administered by placement of the pre-made product upon the burn/wound. The placed pre-made product may serve as a barrier protecting the burn/wound physiochemically, cushioning the wound be and countering evaporation from it.

The hydrogel may be prepared in situ by, for example, spraying its components upon the burn/wound. The spraying may be accompanied by polymerization of the polymers as well as by trapping the fluid in the polymers.

Spraying of the hydrogel in situ upon the burn/wound may be implemented via a spray device. The spray device may produce the polymers by electrospinning. The spray device may produce the polymers by any other suitable process. Any other suitable process may include solution blow spinning. Any other suitable process may include aerosol spraying.

The spray device may carry a supply of the fluid, loaded with wound drying and immunomodulating agents, antibiotic including ethacridine lactate, and any other suitable species, as above.

Hydrogel polymers may themselves be loaded with covalently bonded groups preselected to confer stability and microbicidal and/or other desirable properties upon the hydrogel. The hydrogel polymers may themselves be chemically associated with preselected polar and/or charged species.

The compositions and methods disclosed herein continue to be utilized in research/clinical settings for treatment, and for studies of treatment, of burns/wounds of several types, including radiation burns, diabetic ulcers and bed sores. The open wounds treated by the compositions and methods include open wound types often characterized as chronically non-healing/non-closing open wounds. The closed wounds treated by the compositions and methods include eczema, radiation dermatitis and cellulitis. Use of the compositions and methods has yielded clinically confirmed proper wound closure.

Technical effects of the compositions and methods, as confirmed over numerous clinical cases of optimized wound healing following application of the compositions and methods, include completed wound healing with minimal-to-no scarring of wound sites and patient satisfaction of functional recovery of the repaired tissue. Other aspects and advantages of the compositions and methods-including component amounts; and case of administration; as well as significant positive physiological and psychological benefits accruing to patients-will be further appreciated from the following detailed description.

DETAILED DESCRIPTION OF THE DISCLOSURE

Compositions and methods for therapeutic application to a treatment site are provided. The compositions may be used to perform steps of the methods. The methods may include administration of the compositions to the treatment site.

The compositions may include and the methods may involve compositions of matter for therapeutic application to the treatment site. The compositions may include a composition. The compositions may include a single composition. The term "composition" may include one or more than one composition.

The treatment site may include a region of traumatized skin. The therapeutic application may include application of the composition to the region of traumatized skin. The region of traumatized skin may include an area of disrupted skin integrity. The region of traumatized skin may include an area of damage to the patient's epidermis. The region of traumatized skin may include an area of breach of the epidermis. The region of traumatized skin may include an area evidencing epidermal damage. The region of traumatized skin may include an area presenting epidermal damage.

The region of traumatized skin may include an area of damage to dermal tissue. The region of traumatized skin may include an area presenting damage to dermal tissue. The region of traumatized skin may include an area of damage to sub-dermal tissue. The region of traumatized skin may include an area presenting damage to sub-dermal tissue.

The treatment site may include a burn region. The therapeutic application may include application of the composition to the burn region. The treatment site may include a burn wound site. The therapeutic application may include application of the composition to the burn wound site. The burn region may include a thermal burn. The burn region may include a first-degree burn. The burn region may include a second-degree burn. The burn region may include a third-degree burn. The burn region may include a fourth-degree burn.

The treatment site may include a region of skin exposed to radiation. The therapeutic application may include application of the composition to the region of skin exposed to radiation. The radiation may include sonic radiation. The radiation may include ultrasonic radiation.

The radiation may include electromagnetic radiation. The radiation may include radio-wave radiation. The radiation may include microwave radiation. The radiation may include infrared electromagnetic radiation. The radiation may include visible spectrum electromagnetic radiation. The radiation may include ultraviolet electromagnetic radiation. The radiation may include X-rays. The radiation may include gamma rays. The radiation may involve decay of radioisotopes.

Exposure to the radiation may involve exposure to a natural ambient source of radiation. Exposure to the radiation may involve exposure to sunlight. Exposure to the radiation may involve exposure to artificial light.

Exposure to the radiation may involve use of an energy beam. Exposure to the radiation may involve use of a maser beam. Exposure to the radiation may involve use of a laser beam.

The treatment site may include a region of skin deemed likely to receive radiation therapy. The therapeutic application may include application of the composition to the region of skin deemed likely to receive radiation therapy. The treatment site may include a region of skin that has received radiation therapy. The therapeutic application may include application of the composition to the region of skin that has received radiation therapy. The region of skin that has received radiation therapy may not currently be presenting symptoms of radiation dermatitis. The therapeutic application may include application of the composition to the region of skin prior to the radiation therapy. The region of skin that has received radiation therapy may be presenting symptoms of radiation dermatitis. The therapeutic application may include application of the composition to the region of skin following the radiation therapy. The therapeutic application may include application of the composition to the region of skin closely following the radiation therapy. The therapeutic application may include application of the composition to the region of skin at any time following the radiation therapy.

The radiation therapy may involve X-rays. The radiation therapy may involve beta-ray radiation. The radiation therapy may involve particle beams. The particles may include protons. The particles may include neutrons. The particles may include electrons. The particles may include positrons. The radiation therapy may involve placement of radioisotopes upon the patient's body. The radiation therapy may involve placement of radioisotopes within the patient's body.

The treatment site may include an open wound. The therapeutic application may include application of the composition to the open wound. The open wound may include a diabetic ulcer. The open wound may include a vascular ulcer. The open wound may include a surgical avulsion. The open wound may include a traumatic avulsion. The open wound may include a chronically non-healing open wound. The open wound may include a chronically non-closing open wound. The open wound may include any other suitable type of open wound. Any other suitable type of open wound may include a laceration.

The treatment site may include a region of skin implicated in presentation of symptoms of a closed/non-open burn/wound skin condition. The treatment site may include a region of skin implicated in presentation of a rash. The therapeutic application may include application of the composition to the region of skin implicated in presentation of the rash. The therapeutic application may include application of the composition to the region of skin likely to present with the rash. The region of skin implicated in presentation of the rash may be irritated by contact with a chemical irritant. The region of skin implicated in presentation of the rash may be irritated by contact with a biological irritant. The region of skin implicated in presentation of the rash may be irritated by inhalation of a chemical irritant. The region of skin implicated in presentation of the rash may be irritated by inhalation of a biological irritant. The region of skin implicated in presentation of the rash may be irritated by ingestion of a chemical irritant. The region of skin implicated in presentation of the rash may be irritated by injection of a biological irritant. The region of skin implicated in presentation of the rash may be irritated by injection of a chemical irritant. The region of skin implicated in presentation of the rash may be irritated by ingestion of a biological irritant.

The region of skin implicated in presentation of the rash may not currently be presenting the rash. The therapeutic application may include application of the composition to the region of skin prior to presentation of the rash. The region of skin implicated in presentation of the rash may be presenting the rash. The therapeutic application may include application of the composition to the region of skin following presentation of the rash. The therapeutic application may include application of the composition to the region of skin closely following presentation of the rash. The therapeutic application may include application of the composition to the region of skin at any time following presentation of the rash.

The treatment site may include a region of skin implicated in presentation of eczema symptoms. The therapeutic application may include application of the composition to the region of skin implicated in presentation of eczema symptoms. The region of skin implicated in presentation of eczema symptoms may not currently be presenting eczema symptoms. The therapeutic application may include application of the composition to the region of skin prior to presentation of eczema symptoms. The region of skin implicated in presentation of eczema symptoms may be presenting eczema symptoms. The therapeutic application may include application of the composition to the region of skin following presentation of eczema symptoms. The therapeutic application may include application of the composition to the region of skin closely following presentation of eczema symptoms. The therapeutic application may include application of the composition to the region of skin at any time following presentation of eczema symptoms.

The treatment site may include a region of skin implicated in presentation of cellulitis symptoms. The therapeutic application may include application of the composition to the region of skin implicated in presentation of cellulitis symptoms. The region of skin implicated in presentation of cellulitis symptoms may not currently be presenting cellulitis symptoms. The therapeutic application may include application of the composition to the region of skin prior to presentation of cellulitis symptoms. The region of skin implicated in presentation of cellulitis symptoms may be presenting cellulitis symptoms. The therapeutic application may include application of the composition to the region of skin following presentation of cellulitis symptoms. The therapeutic application may include application of the composition to the region of skin closely following presentation of cellulitis symptoms. The therapeutic application may include application of the composition to the region of skin at any time following presentation of cellulitis symptoms.

The treatment site may include a location on mammalian skin under study in research on burns. The treatment site may include a location on mammalian skin under study in research on wounds. The treatment site may include a location on mammalian skin under study in research on effects of radiation. The treatment site may include a location on mammalian skin under study in research on radiation dermatitis.

The treatment site may include a location on artificial skin under study in research on burns. The treatment site may include a location on artificial skin under study in research on wounds. The treatment site may include a location on artificial skin under study in research on effects of radiation. The treatment site may include a location on artificial skin under study in research on radiation dermatitis.

The composition may include ingredients. The ingredients may include antibiotic. The antibiotic may include ethacridine lactate. The antibiotic may include any other suitable antibiotic. Any other suitable antibiotic may include sulfmethoxazole.

The antibiotic may be present in the composition in a concentration range (wt/wt) of about 0.001% to about 5%. The antibiotic may be present in the composition in a concentration range (wt/wt) of about 0.001% to about 0.01%. The antibiotic may be present in the composition in a concentration range (wt/wt) of about 0.01% to about 0.05%. The antibiotic may be present in the composition in a concentration range (wt/wt) of about 0.05% to about 0.1%. The antibiotic may be present in the composition in a concentration range (wt/wt) of about 0.1% to about 0.2%. The antibiotic may be present in the composition in a concentration range (wt/wt) of about 0.2% to about 0.4%. The antibiotic may be present in the composition in a concentration range (wt/wt) of about 0.4% to about 0.6%. The antibiotic may be present in the composition in a concentration range (wt/wt) of about 0.6% to about 0.8%. The antibiotic may be present in the composition in a concentration range (wt/wt) of about 0.8% to about 1%. The antibiotic may be present in the composition in a concentration range (wt/wt) of about 1% to about 2%. The antibiotic may be present in the composition in a concentration range (wt/wt) of about 2% to about 3%. The antibiotic may be present in the composition in a concentration range (wt/wt) of about 3% to about 4%. The antibiotic may be present in the composition in a concentration range (wt/wt) of about 4% to about 5%. The antibiotic may be present in the composition in a concentration range (wt/wt) of about 5% to about 6%. The antibiotic may be present in the composition in a concentration range (wt/wt) of about 6% to about 7%. The antibiotic may be present in the composition in a concentration range (wt/wt) of about 7% to about 8%. The antibiotic may be present in the composition in a concentration range (wt/wt) of about 8% to about 9%. The antibiotic may be present in the composition in a concentration range (wt/wt) of about 9% to about 10%. The antibiotic may be present in the composition in a concentration range (wt/wt) of about 10% to about 15%. The antibiotic may be present in the composition in a concentration range (wt/wt) of about 15% to about 20%. The antibiotic may be present in the composition in any other suitable concentration range (wt/wt). Any other suitable concentration range of the antibiotic in the composition may include a concentration range (wt/wt) of about 20% to about 25%.

In the composition, concentration of the ethacridine lactate relative to the antibiotic (wt/wt) may be in a range of about 0% to about 1%. In the composition, the concentration of the ethacridine lactate relative to the antibiotic (wt/wt) may be in a range of about 1% to about 10%. In the composition, concentration of the ethacridine lactate relative to the antibiotic (wt/wt) may be in a range of about 10% to about 25%. In the composition, concentration of the ethacridine lactate relative to the antibiotic (wt/wt) may be in a range of about 25% to about 50%. In the composition, concentration of the ethacridine lactate relative to the antibiotic (wt/wt) may be in a range of about 50% to about 75%. In the composition, concentration of the ethacridine lactate relative to the antibiotic (wt/wt) may be in a range of about 75% to about 90%. In the composition, concentration of the ethacridine lactate relative to the antibiotic (wt/wt) may be in a range of about 90% to about 95%. In the composition, concentration of the ethacridine lactate relative to the antibiotic (wt/wt) may be in a range of about 95% to about 100%.

The ethacridine lactate may be present in the composition in a microbiocidal concentration. The ethacridine lactate may be present in the composition at a concentration of about 0.1% (wt/wt). The ethacridine lactate may be present in the composition at a concentration of about 0.2% (wt/wt). The ethacridine lactate may be present in the composition at a concentration of about 0.3% (wt/wt). The ethacridine lactate may be present in the composition at a concentration of about 0.4% (wt/wt). The ethacridine lactate may be present in the composition at a concentration of about 0.5% (wt/wt). The ethacridine lactate may be present in the composition at a concentration of about 1% (wt/wt). The ethacridine lactate may be present in the composition at a concentration of about 1.5% (wt/wt). The ethacridine lactate may be present in the composition at a concentration of about 2% (wt/wt). The ethacridine lactate may be present in the composition at a concentration of about 2.5% (wt/wt).

The ingredients may include non-water-soluble species. The ingredients may include hydrophobic compounds. The ingredients may include hydrophobic organic compounds. The ingredients may include hydrophobic polymers. The ingredients may include high-molecular weight (MW) non-water-soluble ingredients. The ingredients may include long-chain organic polymers. The ingredients may include long-chain polyunsaturated hydrocarbons. The ingredients may include long-chain waxy esters.

The long-chain/high-MW ingredients may have higher melting points than melting points of intermediate-length-chain/intermediate-MW ingredients. The intermediate-length-chain/intermediate-MW ingredients may have higher melting points than melting points of lower MW ingredients. Manufacture of the unitary product may require blending together of multiple different-temperature molten sets of ingredients. Such different temperatures and temperature ranges for the molten ingredient-sets may include about room temperature to about 85° F. for low-T melting point ingredients; about 95° F. to about 120° F. for mid-T melting point ingredients; and about 125° F. to about 135° F. for high-T melting point ingredients.

Preparation of the treatment site prior to the therapeutic application may include cleansing of the burn/wound. Preparation of the treatment site prior to the therapeutic application may include debridement of the burn/wound.

The therapeutic application may include application, upon the treatment site, of the ointment that includes the composition. The therapeutic application may include application, upon the treatment site, of the cream that includes the composition.

The composition may include a barrier. The barrier may form when the composition is applied to the treatment site.

The ingredients may form the barrier when the composition is applied to the treatment site. The barrier may be formed upon the treatment site. The composition may include the ingredients that may form the barrier. The barrier may be formed by the ingredients constituting the barrier. The composition may include the ingredients constituting the barrier. The barrier may be formed by the ingredients assembling the barrier. The composition may include the ingredients assembling the barrier. The barrier may include an occlusive agent. The barrier may include an occlusive surface. The composition may include the occlusive agent. The composition may include the occlusive surface.

The barrier may include a physical barrier. The barrier may include a chemical barrier. The barrier may include a physiochemical barrier. The barrier may provide physical protection to the treatment site. The barrier may provide chemical protection to the treatment site. The barrier may include a barrier against evaporation from the treatment site. The barrier may include a barrier limiting evaporation from the treatment site.

The ingredients may include a metal-containing species. The composition may include a metal-containing species. The barrier may include the metal-containing species. The metal-containing species may include nanoparticles of the metal-containing species. The metal-containing species may include zinc. The metal-containing species may include any other suitable metal. Any other suitable metal may include silver. The metal-containing species may include metal oxide.

The ingredients may include a moisture-modulating agent. The composition may include a moisture-modulating agent. The barrier may include the moisture-modulating agent. The moisture-modulating agent may have antimicrobial properties. The moisture-modulating agent may have other suitable properties. Other suitable properties may include anesthetic properties.

The moisture-modulating agent may include an occlusive agent. The occlusive agent may include beeswax. The occlusive agent may include any other suitable occlusive agent. Any other suitable occlusive agent may include lanolin.

The moisture-modulating agent may include a humectant agent. The humectant agent may include honey. The humectant agent may include propylene glycol. The humectant agent may include any other suitable humectant agent. Any other suitable humectant agent may include aloe vera. Any other suitable humectant agent may include hyaluronic acid.

The moisture-modulating agent may include an emollient agent. The emollient agent may include jojoba oil. The emollient agent may include any other suitable emollient agent. Any other suitable emollient agent may include castor oil.

The ingredients may include clove oil. The clove oil may include eugenol. The ingredients may include nutmeg oil. The nutmeg oil may include eugenol. The ingredients may include olive oil. The ingredients may include tea tree oil. The ingredients may include any other suitable ingredient. Any other suitable ingredient may include vitamin E oil. Any other suitable ingredient may include calendula oil.

The moisture-modulating agent may provide transport of the antibiotic to a surface of the treatment site. The moisture-modulating agent may provide transport of the antibiotic from the composition to the surface of the treatment site. The moisture-modulating agent may provide transport to the surface of the treatment site of the antibiotic from within a bulk of the composition applied to the treatment site. The moisture-modulating agent may provide transport of the antibiotic from the barrier to the surface of the treatment site.

The moisture-modulating agent may provide transport of the metal-containing species to the surface of the treatment site. The moisture-modulating agent may provide transport of the metal-containing species from the composition to the surface of the treatment site. The moisture-modulating agent may provide transport to the surface of the treatment site of the metal-containing species from within the bulk of the composition applied to the treatment site. The moisture-modulating agent may provide transport of the metal-containing from the barrier to the surface of the treatment site.

The metal-containing species may contribute to stabilization of the antibiotic in the composition. The metal-containing species may contribute to healing of the treatment site. The metal-containing species may contribute to drying of the treatment site. The metal-containing species may contribute to debridement of the treatment site. The metal-containing species may contribute to antiseptic cleansing of the treatment site. The metal-containing species contributing to antiseptic cleansing of the treatment site may supplement antimicrobial activity of the antibiotic.

The metal-containing species may provide an ion that serves as a ligand in a treatment-site metalloprotein. The metalloprotein may include a metalloprotease. The metalloprotease may degrade necrotic tissue. The metalloprotease may facilitate wound repair and new tissue growth, by digesting wound-site extracellular matrix. The metalloprotease may serve as a microbicide. The metalloprotease serving as a microbicide may supplement antimicrobial activity of the antibiotic.

The ingredients may include hydrophilic compounds. The ingredients may include hydrophilic organic compounds. The ingredients may include hydrophilic polymers. The ingredients may include high-molecular weight hydrophilic polymer ingredients. The ingredients may include precursors to hydrophilic polymer species, the hydrophilic polymer species preselected to form, with fluid, a hydrogel. The hydrogel may include a hydrogel matrix. The ingredients may include the high-molecular weight hydrophilic polymer species preselected to form, with the fluid, the hydrogel matrix. The ingredients may include high-molecular weight hydrophilic polymer ingredients preselected to trap the fluid within and as part of the hydrogel matrix. The fluid may include water. The fluid may include plasma. The fluid may include a plasma analog. The fluid may carry cell fragments such as platelets. The fluid may carry fibrin.

The hydrogel may include the antibiotic. The fluid may include the antibiotic. The fluid may contribute to stabilization of the antibiotic in the hydrogel. The hydrogel may include the metal-containing species. The fluid may include the metal-containing species. The hydrogel may include the occlusive agent. The fluid may include the occlusive agent. The hydrogel may include the humectant agent. The fluid may include the humectant agent. The hydrogel may include the emollient agent. The fluid may include the emollient agent.

The barrier may include the hydrogel. The hydrogel, when applied to the treatment site, may constitute the barrier. The hydrogel may include the moisture-modulating agent. The moisture-modulating agent may include the hydrophilic, fluid-trapping polymer. The hydrophilic, fluid-trapping polymer may include antimicrobial species along its length.

Antimicrobial species included along the hydrophilic, fluid-trapping polymer may include charged groups. The antimicrobial species included along the hydrophilic, fluid-trapping polymer may include polar groups. The antimicrobial species included along the hydrophilic, fluid-trapping polymer may include functional groups preselected for their antimicrobial properties.

The therapeutic application may include application upon the treatment site of the hydrogel. Application upon the treatment site of the hydrogel may include placement upon the treatment site of a pre-made hydrogel.

The hydrogel may draw exudate away from the treatment site. The hydrogel may deliver hydrogel fluid contents to the treatment site.

Application upon the treatment site of the hydrogel may include spraying onto the treatment site a spray constituted to form the barrier in situ upon the treatment site. The spraying may be implemented by the spray device. The spray device may polymerize in situ the precursor ingredients of the high-molecular weight hydrophilic polymer. The spray device may deliver upon the treatment site other hydrogel ingredients (fluid, antibiotic, moisture-modulating agent, etc.) in tandem with the polymerizing high-molecular weight hydrophilic polymer, to constitute the hydrogel. The spray device may deliver upon the treatment site the in situ-formed hydrogel.

Compositions and methods for therapeutic application to a wound site are provided. The compositions may be used to perform steps of the methods. The methods may include preparation of the wound site prior to administration of the compositions. The methods may include administration of the compositions to the wound site. The compositions and methods may include administration of the compositions to the wound site.

The compositions may include and the methods may involve compositions of matter for therapeutic application to the wound site. The compositions may include a composition. The compositions may include a single composition. The term "composition" may include one or more than one composition.

The composition may include ingredients presented above for therapeutic application to the treatment site. The therapeutic application may include therapeutic applications presented above for application to the treatment site.

The composition may include the antibiotic, including ethacridine lactate, characterized as presented above with respect to the treatment site.

The composition, when applied to a wound bed of the wound site, may include a physicochemical barrier. The physicochemical barrier upon the wound bed may be compositionally characterized by compositional descriptions of the physicochemical barrier presented with respect to the treatment site. The physicochemical barrier upon the wound bed may be functionally characterized by functional descriptions of the physicochemical barrier presented with respect to the treatment site.

The physicochemical barrier upon the wound bed may include an organic polymer species. The composition may include the organic polymer species. The organic polymer species may provide transport of the antibiotic to the wound bed.

The physicochemical barrier upon the wound bed may include a chemical species stabilizing the antibiotic. The composition may include the chemical species stabilizing the antibiotic. The organic polymer species may provide transport, to the wound bed, of the chemical species stabilizing the antibiotic.

Compositions and methods for therapeutic application to a burn region are provided. The compositions may be used to perform steps of the methods. The methods may include preparation of the burn region prior to administration of the compositions. The methods may include administration of the compositions to the burn region. The compositions and methods may include administration of the compositions to the burn region.

The compositions may include and the methods may involve compositions of matter for therapeutic application to the burn region. The compositions may include a composition. The compositions may include a single composition. The term "composition" may include one or more than one composition.

The composition may include ingredients presented above for therapeutic application to the treatment site. The therapeutic application may include therapeutic applications presented above for application to the treatment site.

The composition may include the antibiotic, including ethacridine lactate, characterized as presented above with respect to the treatment site.

The composition, when applied to a surface of the burn region, may include a physicochemical barrier. The physicochemical barrier may overlie the burn region. The physicochemical barrier overlying the burn region may be compositionally characterized by compositional descriptions of the physicochemical barrier presented above with respect to the treatment site. The physicochemical barrier overlying the burn region may be functionally characterized by functional descriptions of the physicochemical barrier presented above with respect to the treatment site.

The physicochemical barrier overlying the burn region may serve as a barrier against evaporation from the surface. The physicochemical barrier overlying the burn region may include a hydrophobic polymer species forming an occlusive layer. The composition may include the hydrophobic polymer species.

The composition may include a moisture-modulating agent. The moisture-modulating agent may provide transport, to the surface, of the antibiotic. The moisture-modulating agent may provide transport, to the surface from the physicochemical barrier overlying the burn region, of the antibiotic.

The physicochemical barrier overlying the burn region may include a hydrophilic polymer species. The composition may include the hydrophilic polymer species. The hydrophilic polymer species, together with fluid, may form a hydrogel.

The therapeutic application may include spraying onto the surface a spray constituted to form, in situ upon the surface, the physicochemical barrier overlying the burn region. The physicochemical barrier overlying the burn region may include the hydrogel. The hydrogel may include the physicochemical barrier overlying the burn region.

Initial studies of use of the compositions and methods presented herein on human subjects are underway. A porcine burn study is in development. The initial human studies have yielded wound closure with minimal-to-no scarring and with patient/clinician satisfaction regarding functionality of repaired tissue.

Expanded studies are continuing and further studies are planned, expected to focus on use of the compositions and methods disclosed herein to burn/wound treatment.

All references cited in the present application are incorporated in their entirety herein by reference to the extent not inconsistent herewith.

Thus, compositions and methods for burn/wound treatment have been provided. Persons skilled in the art will appreciate that the present invention can be practiced by other than the described embodiments, which are presented for purposes of illustration rather than of limitation. The present invention is limited only by the claims that follow.

What is claimed is:

1. A composition of matter for therapeutic application to a treatment site, the composition comprising:
   antibiotic comprising ethacridine lactate; and,
   when applied to the treatment site, a physicochemical barrier comprising a moisture-modulating agent.

2. The composition of claim 1 wherein concentration of the ethacridine lactate is in a range of about 0.01% to about 5% (wt/wt).

3. The composition of claim 1 wherein concentration of the ethacridine lactate is about 1% (wt/wt).

4. The composition of claim 1 wherein the moisture-modulating agent provides transport, to the treatment site, of the antibiotic.

5. The composition of claim 4 wherein the moisture-modulating agent includes a humectant agent.

6. The composition of claim 4 wherein the moisture-modulating agent includes an emollient agent.

7. The composition of claim 1 wherein the barrier includes an occlusive layer.

8. The composition of claim 1 wherein the barrier includes a metal-containing species.

9. The composition of claim 8 wherein the metal-containing species includes nanoparticles of the metal-containing species.

10. The composition of claim 8 wherein the moisture-modulating agent provides transport, to the treatment site, of the metal-containing species.

11. The composition of claim 1 wherein the therapeutic application includes application upon the treatment site of ointment that includes the composition.

12. The composition of claim 1 wherein the therapeutic application includes application upon the treatment site of cream that includes the composition.

13. The composition of claim 1 wherein the barrier includes a hydrogel.

14. The composition of claim 13 wherein the moisture-modulating agent includes a hydrophilic polymer species.

15. The composition of claim 1 wherein the therapeutic application includes placement upon the treatment site of a pre-made hydrogel.

16. The composition of claim 1 wherein the therapeutic application includes spraying onto the treatment site a spray constituted to form the barrier in situ upon the treatment site.

17. The composition of claim 16 wherein the spraying includes spraying implemented by a spray device.

18. The composition of claim 1 wherein the treatment site includes an open wound.

19. The composition of claim 1 wherein the treatment site includes a burn region.

20. The composition of claim 1 wherein the treatment site includes a region of skin exposed to radiation.

21. The composition of claim 1 wherein the treatment site includes a region of skin implicated in presentation of eczema symptoms.

* * * * *